(12) United States Patent
Salamone et al.

(10) Patent No.: US 8,030,423 B2
(45) Date of Patent: Oct. 4, 2011

(54) MULTI-ARMED MACROMONOMERS

(76) Inventors: Joseph C. Salamone, San Antonio, TX (US); Jay F. Kunzler, Canandaigua, NY (US)

(*) Notice: Subject to any disclaimer, the term of this patent is extended or adjusted under 35 U.S.C. 154(b) by 137 days.

(21) Appl. No.: 12/352,616

(22) Filed: Jan. 13, 2009

(65) Prior Publication Data
US 2009/0192275 A1 Jul. 30, 2009

Related U.S. Application Data

(60) Provisional application No. 61/023,461, filed on Jan. 25, 2008.

(51) Int. Cl.
C08F 30/08 (2006.01)
G02B 1/04 (2006.01)

(52) U.S. Cl. .............. 526/279; 528/32; 528/33; 528/37; 523/107; 526/258; 526/303.1; 526/317.1; 526/319; 526/320

(58) Field of Classification Search .......................... None
See application file for complete search history.

(56) References Cited

U.S. PATENT DOCUMENTS

| | | | |
|---|---|---|---|
| 3,408,429 A | 10/1968 | Wichterle | |
| 3,578,726 A * | 5/1971 | Bostick et al. | 528/34 |
| 3,660,545 A | 5/1972 | Wichterle | |
| 3,997,497 A * | 12/1976 | Itoh et al. | 528/33 |
| 4,113,224 A | 9/1978 | Clark et al. | |
| 4,136,250 A | 1/1979 | Mueller et al. | |
| 4,153,641 A | 5/1979 | Deichert et al. | |
| 4,197,266 A | 4/1980 | Clark et al. | |
| 4,327,203 A | 4/1982 | Deichert et al. | |
| 4,355,147 A | 10/1982 | Deichert et al. | |
| 4,555,732 A | 11/1985 | Tuhro | |
| 4,659,782 A | 4/1987 | Spinelli | |
| 4,740,533 A | 4/1988 | Su et al. | |
| 4,910,277 A | 3/1990 | Bambury et al. | |
| 4,954,587 A | 9/1990 | Mueller | |
| 5,010,141 A | 4/1991 | Mueller | |
| 5,019,628 A | 5/1991 | Spinelli | |
| 5,034,461 A | 7/1991 | Lai et al. | |
| 5,070,215 A | 12/1991 | Bambury et al. | |
| 5,079,319 A | 1/1992 | Mueller | |
| 5,244,981 A | 9/1993 | Seidner et al. | |
| 5,260,000 A | 11/1993 | Nandu et al. | |
| 5,270,418 A | 12/1993 | Kunzler et al. | |
| 5,271,875 A | 12/1993 | Appleton et al. | |
| 5,310,779 A | 5/1994 | Lai | |
| 5,314,961 A | 5/1994 | Anton et al. | |
| 5,321,108 A | 6/1994 | Künzler et al. | |
| 5,331,067 A | 7/1994 | Seidner et al. | |
| 5,358,995 A | 10/1994 | Lai et al. | |
| 5,371,147 A | 12/1994 | Spinelli et al. | |
| 5,387,662 A | 2/1995 | Künzler et al. | |
| 5,527,935 A * | 6/1996 | Stepp et al. | 556/445 |
| 5,637,668 A * | 6/1997 | Graiver et al. | 528/33 |
| 5,663,245 A | 9/1997 | Kennedy et al. | |
| 5,760,145 A * | 6/1998 | Herzig et al. | 525/478 |
| 7,297,160 B2 | 11/2007 | Salamone et al. | |
| 2007/0197733 A1 | 8/2007 | Salamone et al. | |

FOREIGN PATENT DOCUMENTS

WO WO 96/31792 10/1996

OTHER PUBLICATIONS

"Synthesis of Starshaped Polydimethylsiloxane containing SiO2 Core Units" authored by Ogawa et al., and published in Macromol. Chem. Phys. (1994) 195,1973-1983.*

"Synthesis of Branched Polysiloxanes with Controlled Brancning and Functionalization by Anionic Ring-Opening Polymerization" authored by Chojnowski et al., and published in Macromolecules (2003) 36, 3890-3897.*

Lai, Yu-Chin, "The Role of Bulky Polysiloxanylalkyl Methacryates in Polyurethane-Polysiloxane Hydrogels", *Journal of Applied Polymer Science*, vol. 60, 1193-1199 (1996).

* cited by examiner

*Primary Examiner* — Marc Zimmer

(74) *Attorney, Agent, or Firm* — Glenn D. Smith; M. Carmen & Associates, PLLC

(57) ABSTRACT

Multi-armed macromonomers containing multiple side chains attached to a siloxy-containing core terminated on each end with one or more first substantially linear polysiloxane radicals having a polymerizable ethylenically unsaturated-containing terminal group, wherein each side chain comprises a second substantially linear polysiloxane radical having a polymerizable ethylenically unsaturated-containing terminal group are disclosed. Biomedical devices such as contact lenses formed from the multi-armed macromonomers are also disclosed.

14 Claims, No Drawings

MULTI-ARMED MACROMONOMERS

PRIORITY CLAIMS TO PRIOR APPLICATIONS

This application claims the benefit of Provisional Patent Application No. 61/023,461 filed Jan. 25, 2008.

BACKGROUND OF THE INVENTION

1. Technical Field

The present invention generally relates to multi-armed macromonomers such as multi-armed polysiloxy macromonomers and their use as biomedical devices.

2. Description of Related Art

Biomedical devices such as ophthalmic lenses made from siloxy-containing materials have been investigated for a number of years. Such materials can generally be sub-divided into two major classes, namely hydrogels and non-hydrogels. Hydrogels can absorb and retain water in an equilibrium state whereas non-hydrogels do not absorb appreciable amounts of water. Regardless of their water content, both hydrogel and non-hydrogel siloxy and/or fluorinated contact lenses tend to have relatively hydrophobic, non-wettable surfaces.

Hydrogels represent a desirable class of materials for many biomedical applications, including contact lenses and intraocular lenses. Hydrogels are hydrated, crosslinked polymeric systems that contain water in an equilibrium state. Silicone hydrogels are a known class of hydrogels and are characterized by the inclusion of a siloxy-containing material. Typically, a siloxy-containing monomer is copolymerized by free radical polymerization with a hydrophilic monomer, with either the siloxy-containing monomer or the hydrophilic monomer functioning as a crosslinking agent (a crosslinker being defined as a monomer having multiple polymerizable functionalities) or a separate crosslinker may be employed. An advantage of silicone hydrogels over non-silicone hydrogels is that the silicone hydrogels typically have higher oxygen permeability due to the inclusion of the siloxy-containing monomer. Because such hydrogels are based on free radical polymerization of monomers containing a crosslinking agent, these materials are thermosetting polymers.

In the field of biomedical devices such as contact lenses, various physical and chemical properties such as, for example, oxygen permeability, wettability, material strength and stability are but a few of the factors that must be carefully balanced in order to provide a useable contact lens. For example, since the cornea receives its oxygen supply exclusively from contact with the atmosphere, good oxygen permeability is a critical characteristic for any contact lens material. Wettability also is important in that, if the lens is not sufficiently wettable, it does not remain lubricated and therefore cannot be worn comfortably in the eye. Accordingly, the optimum contact lens would have at least both excellent oxygen permeability and excellent tear fluid wettability.

U.S. Pat. No. 5,019,628 ("the '628 patent") discloses star polymers containing a core of highly crosslinked segments of difunctional acrylates or copolymers of monofunctional and difunctional acrylates, and attached to the core at least 5 linear copolymeric arms derived from one or more (meth)acrylate monomers, wherein about 5 to 100% by weight of the (meth) acrylate monomers from which the arms are derived are in the form of a block consisting essentially of one or more monofunctional monomeric polysiloxanylalkyl ester units. The '628 patent further discloses that the star polymers can be used in combination with other polymers to improve the properties of the other polymers such as to impart an improved combination of oxygen permeability and hardness in polysiloxanylalkyl acrylic polymers used for contact lens applications.

U.S. Pat. No. 5,244,981 ("the '981 patent") and U.S. Pat. No. 5,331,067 ("the '067 patent") disclose silicone-containing acrylic polymers obtained from the copolymerization of pre-formed macromonomers and/or acrylic star polymers with monomers of a polymer matrix, for example, silicone acrylates, esters of acrylic and/or methacrylic acid ((meth) acrylates) and contact lenses made from these polymers. The '981 and '067 patents define the term "macromonomer" to describe pre-formed linear silicone-containing acrylic homopolymers, block polymers or random copolymers that preferably have a polymerizable group at one end of the polymer chain.

U.S. Pat. No. 5,314,961 ("the '961 patent") discloses compositions containing macromonomers, graft polymers and acrylic star polymers dispersed or copolymerized throughout a polymer matrix to enhance the characteristics of hard and soft contact lenses. The '961 patent further discloses the star polymers contain a highly crosslinked core and attached to the core at least 5 linear polymeric arms having at least one substantially hydrophilic block preferably derived from at least about 20 to 25% by weight of hydrophilic acrylic-type monomers and at least one substantially hydrophobic, permeable block derived from at least about 50% by weight of at least one polysiloxanylalkyl ester of an alpha, beta, unsaturated ester (silicone acrylate). The highly crosslinked core of the star polymer can be highly crosslinked segments of difunctional acrylates, copolymers of monofunctional and difunctional acrylates or a crosslinked polysiloxy core derived from a multifunctional crosslinkable silicone-containing group, such as a polyalkoxysilyl group. In addition, the '961 patent defines the term "macromonomer" to describe preformed linear silicone-containing acrylic polymers which may be used to produce hydrated oxygen permeable compositions.

U.S. Pat. No. 7,297,160 discloses high refractive-index, hydrophilic, arylsiloxy-containing monomers, macromonomers, and polymers, and ophthalmic devices comprising such polymers.

It would be desirable to provide improved biomedical devices formed from a siloxy macromonomer material that exhibit suitable physical and chemical properties, e.g., oxygen permeability and wettability, for prolonged contact with the body while also being biocompatible. It would also be desirable to provide improved biomedical devices that are easy to manufacture in a simple, cost effective manner.

SUMMARY OF THE INVENTION

In accordance with one embodiment of the present invention, a multi-armed macromonomer is provided comprising multiple side chains attached to a siloxy-containing core terminated on each end with one or more first substantially linear polysiloxane radicals having a polymerizable ethylenically unsaturated-containing terminal group, wherein each side chain comprises a second substantially linear polysiloxane radical having a polymerizable ethylenically unsaturated-containing terminal group.

In accordance with a second embodiment of the present invention, a multi-armed macromonomer is provided comprising multiple side chains attached to a polysiloxy-containing core terminated on each end with one or more first substantially linear polysiloxane radicals having a polymerizable ethylenically unsaturated-containing terminal group, wherein each side chain comprises a second substantially linear polysiloxane radical having a polymerizable ethylenically unsaturated-containing terminal radical.

In accordance with a third embodiment of the present invention, a multi-armed macromonomer of the general formula is provided:

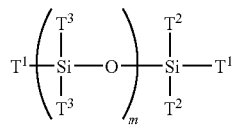

wherein each $T^1$, $T^2$, $T^3$ and m is as defined herein.

In accordance with a fourth embodiment of the present invention, a copolymer is provided comprising a polymerization product of a monomeric mixture comprising one or more multi-armed macromonomers comprising multiple side chains attached to a siloxy-containing core terminated on each end with one or more first substantially linear polysiloxane radicals having a polymerizable ethylenically unsaturated-containing terminal group, wherein each side chain comprises a second substantially linear polysiloxane radical having a polymerizable ethylenically unsaturated-containing terminal group.

In accordance with a fifth embodiment of the present invention, a biomedical device is provided comprising a polymerization product of a monomeric mixture comprising (a) one or more multi-armed macromonomers comprising multiple side chains attached to a siloxy-containing core terminated on each end with one or more first substantially linear polysiloxane radicals having a polymerizable ethylenically unsaturated-containing terminal group, wherein each side chain comprises a second substantially linear polysiloxane having a polymerizable ethylenically unsaturated-containing terminal group; and (b) one or more biomedical device-forming monomers.

In accordance with a sixth embodiment of the present invention, a biomedical device is provided comprising a polymerization product of a monomeric mixture comprising one or more multi-armed macromonomers of the general formula:

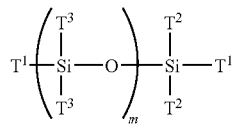

wherein m, $T^1$, $T^2$ and $T^3$ are as defined herein.

The multi-armed macromonomers of the present invention advantageously increase the free volume between the molecules due to steric hindrance of two or more polymerizable polysiloxanyl macromonomers covalently bonded to a silicon atom. This steric hindrance will increase as the number of polysiloxanyl macromolecules is increased. Such steric hindrance, caused by repulsion of the polysiloxanyl chains, would increase the free volume surrounding the silicon atoms to which the macromolecular polysiloxanyl chains are attached, thereby increasing the gas permeability relative to linear polysiloxanyl macromolecules. Copolymers derived from one or more of the multi-armed macromonomers of the present invention are believed to advantageously provide improved biomedical devices exhibiting increased oxygen permeability, with an overall lower density than related linear polysiloxanyl macromolecules. In addition, the multi-armed macromonomers of the present invention employ well defined, easy to characterize siloxy-containing cores which yield relatively simple core architectures. In this manner, the multi-armed macromonomers can be synthesized in a simple, cost efficient process.

DETAILED DESCRIPTION OF THE PREFERRED EMBODIMENTS

The present invention is directed to multi-armed macromonomers and copolymers useful as biomedical devices intended for direct contact with body tissue or fluid. Representative examples of biomedical devices include, but are not limited to, artificial ureters, diaphragms, intrauterine devices, heart valves, catheters, denture liners, prosthetic devices, ophthalmic lens applications, where the lens is intended for direct placement in or on the eye, such as, for example, intraocular devices and contact lenses. The devices can provide optical correction, wound care, drug delivery, diagnostic functionality or cosmetic enhancement or effect or a combination of these properties. As used herein, the term "ophthalmic device" refers to devices that reside in or on the eye. Useful ophthalmic devices include, but are not limited to, ophthalmic lenses such as soft contact lenses, e.g., a soft, hydrogel lens (e.g., silicone hydrogels), soft, non-hydrogel lens and the like; hard contact lenses, e.g., a hard, gas permeable lens material and the like; intraocular lenses; overlay lenses; ocular inserts; optical inserts and the like. As is understood by one skilled in the art, a lens is considered to be "soft" if it can be folded back upon itself without breaking. The preferred biomedical devices are ophthalmic devices, particularly contact lenses, most particularly contact lenses made from silicone hydrogels.

The multi-armed macromonomer of the present invention comprises multiple side chains attached to a siloxy-containing core terminated on each end with one or more substantially linear polysiloxane radicals having a polymerizable ethylenically unsaturated-containing terminal group, and wherein each side chain comprises a substantially linear polysiloxane radical having a polymerizable ethylenically unsaturated-containing terminal group. In one embodiment, the multi-armed macromonomer comprises multiple side chains attached to a polysiloxy-containing core terminated on each end with one or more substantially linear polysiloxane radicals having a polymerizable ethylenically unsaturated-containing terminal group and wherein each side chain comprises a substantially linear polysiloxane radical having a polymerizable ethylenically unsaturated-containing terminal group. In another embodiment, the multi-armed macromonomer comprises multiple side chains attached to a non-crosslinked siloxy-containing core terminated on each end with one or more substantially linear polysiloxane radicals having a polymerizable ethylenically unsaturated-containing terminal group. The terms "non-crosslinked siloxy-containing core" or "non-crosslinked polysiloxy-containing core" as used herein is meant a core which does not contain, for example, crosslinked segments in the core such as crosslinked segments of difunctional acrylates or copolymers of monofunctional and difunctional acrylates, but which contains reactive silicon groups. Such non-crosslinked cores are typically non-ethylenically unsaturated containing cores. In another embodiment, the multi-armed macromonomer of the present invention comprises multiple side chains attached to a non-functional siloxy- or polysiloxy-containing core terminated on each end with one or more substantially linear polysiloxane radicals having a polymerizable ethylenically unsaturated-containing terminal group.

The arms of the multi-armed macromonomers of the present invention, i.e., the multiple side chains and terminal groups, are endcapped with the same or different polymerizable ethylenically unsaturated-containing radical, e.g., group "A" as set forth in $T^1$, $T^2$ and $T^3$ for Formula I below. Representative examples of a "polymerizable ethylenically unsaturated-containing radical" include, by way of example, (meth)acrylate-containing radicals, (meth)acrylamide-containing radicals, vinylcarbonate-containing radicals, vinylcarbamate-containing radicals, styrene-containing radicals, vinyl-containing radicals, vinyl ether-containing radicals, maleimide-containing radicals, itaconate-containing radicals, fumarate-containing radicals and the like. As used herein, the term "(meth)" denotes an optional methyl substituent. Thus, terms such as "(meth)acrylate" denotes either methacrylate or acrylate, and "(meth)acrylic acid" denotes either methacrylic acid or acrylic acid. If desired, the polymerizable ethylenically unsaturated-containing radical can further contain segments of hydrophilic units. In one embodiment, the arms of the multi-armed macromonomers of the present invention are endcapped with a (meth)acrylate-containing radical.

In one embodiment, a polymerizable ethylenically unsaturated-containing radical is represented by the general formula:

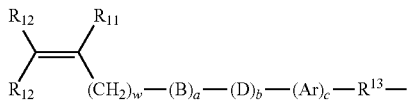

wherein $R^{11}$ is hydrogen or methyl;

each $R^{12}$ is independently hydrogen, an alkyl radical having 1 to 6 carbon atoms, or a —CO—Y—$R^{14}$ radical wherein Y is —O—, —S— or —NH— and $R^{14}$ is an alkyl radical having 1 to about 10 carbon atoms;

$R^{13}$ is a divalent alkenyl radical having 1 to about 12 carbon atoms;

B denotes —O— or —NH—; D denotes —CO—, —OCO— or —COO;

Ar denotes an aromatic radical having 6 to about 30 carbon atoms;

w is 0 to 6; a is 0 or 1; b is 0 or 1; and c is 0 or 1.

A representative class of multi-armed macromonomers of the present invention is represented by the structure of Formula I:

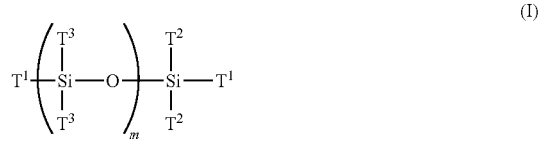

wherein each $T^1$ is independently

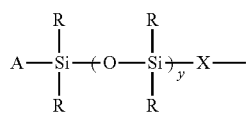

and wherein m is at least 1 and preferably from 1 to about 100 and more preferably from about 1 to about 25; or m is at least 2, preferably from 2 to about 100 and more preferably from about 2 to about 25; y is at least 1 and preferably from 1 to 100; R is independently a monovalent hydrocarbon radical having 1 to 30 carbon atoms which may include ether linkages therebetween including, by way of example, a straight or branched, substituted or unsubstituted $C_1$-$C_{30}$ alkyl group, a substituted or unsubstituted $C_3$-$C_{30}$ cycloalkyl group, a substituted or unsubstituted $C_3$-$C_{30}$ cycloalkylalkyl group, a substituted or unsubstituted $C_3$-$C_{30}$ cycloalkenyl group, a substituted or unsubstituted $C_5$-$C_{30}$ aryl group, and a substituted or unsubstituted $C_5$-$C_{30}$ arylalkyl group; a halogen substituted monovalent hydrocarbon radical having 1 to about 20 carbon atoms which may include ether linkages therebetween including, by way of example, a $C_1$-$C_{30}$ fluoro-substituted alkyl group or alkenyl group, a substituted or unsubstituted $C_5$-$C_{30}$ heteroaryl group; a substituted or unsubstituted $C_3$-$C_{30}$ heterocyclic ring; a substituted or unsubstituted $C_4$-$C_{30}$ heterocycloalkyl group; or a substituted or unsubstituted $C_6$-$C_{30}$ heteroarylalkyl group; a $C_1$-$C_{20}$ ester group; an ether or polyether-containing group, e.g., an alkyl ether, cycloalkyl ether, cycloalkylalkyl ether, cycloalkenyl ether, aryl ether, arylalkyl ether, polyalkyl ether, polycycloalkyl ether, polycycloalkylalkyl ether, polycycloalkenyl ether, polyaryl ether or polyarylalkyl ether; an alkyl- or arylamide group; an alkyl- or arylamine group; a substituted or unsubstituted $C_1$-$C_{30}$ alkoxy group; and combinations thereof; X is —O— and A is independently a polymerizable ethylenically unsaturated-containing radical as defined herein.

$T^2$ and $T^3$ are independently hydrogen, a straight or branched, substituted or unsubstituted $C_1$-$C_{30}$ alkyl group, a substituted or unsubstituted $C_3$-$C_{30}$ cycloalkyl group, a substituted or unsubstituted $C_3$-$C_{30}$ cycloalkylalkyl group, a substituted or unsubstituted $C_3$-$C_{30}$ cycloalkenyl group, a substituted or unsubstituted $C_5$-$C_{30}$ aryl group, and a substituted or unsubstituted $C_5$-$C_{30}$ arylalkyl group, a $C_1$-$C_{30}$ fluoro-substituted alkyl group or alkenyl group; a $C_1$-$C_{20}$ ester group; an ether or polyether-containing group; an alkyl- or arylamide group; an alkyl- or arylamine group; a substituted or unsubstituted $C_1$-$C_{30}$ alkoxy group; a substituted or unsubstituted $C_5$-$C_{30}$ heteroaryl group; a substituted or unsubstituted $C_3$-$C_{30}$ heterocyclic ring; a substituted or unsubstituted $C_4$-$C_{30}$ heterocycloalkyl group; a substituted or unsubstituted $C_6$-$C_{30}$ heteroarylalkyl group; a vinyl group; a $C_5$-$C_{30}$ fluoroalkyl or fluoroaryl group and combinations thereof and further wherein at least one of $T^2$ and at least one of $T^3$ in each repeating unit are independently of the same formula as $T^1$.

In one embodiment, two R groups attached to the same silicon atom can be the same, but different from two R groups attached to another silicon atom. In another embodiment, all R groups are the same.

Representative examples of alkyl groups for use herein include, by way of example, a straight or branched alkyl chain radical containing carbon and hydrogen atoms of from 1 to about 30 carbon atoms and preferably from 1 to about 6 carbon atoms with or without unsaturation, to the rest of the molecule, e.g., methyl, ethyl, n-propyl, 1-methylethyl(isopropyl), n-butyl, n-pentyl, etc., and the like.

Representative examples of fluoroalkyl groups for use herein include, by way of example, a straight or branched alkyl group as defined herein having one or more fluorine atoms attached to the carbon atom, e.g., —$CF_3$, —$CF_2CF_3$, —$CH_2CF_3$, —$CH_2CF_2H$, —$CF_2H$ and the like.

Representative examples of cycloalkyl groups for use herein include, by way of example, a substituted or unsubstituted non-aromatic mono or multicyclic ring system of about 3 to about 30 carbon atoms such as, for example, cyclopropyl, cyclobutyl, cyclopentyl, cyclohexyl, perhydronapththyl, adamantyl and norbornyl groups, bridged cyclic groups or sprirobicyclic groups, e.g., spiro-(4,4)-non-2-yl and the like, optionally containing one or more heteroatoms, e.g., O and N, and the like.

Representative examples of cycloalkylalkyl groups for use herein include, by way of example, a substituted or unsubstituted cyclic ring-containing radical containing from about 3 to about 30 carbon atoms directly attached to the alkyl group which are then attached to the main structure of the monomer at any carbon from the alkyl group that results in the creation of a stable structure such as, for example, cyclopropylmethyl, cyclobutylethyl, cyclopentylethyl and the like, wherein the cyclic ring can optionally contain one or more heteroatoms, e.g., O and N, and the like.

Representative examples of cycloalkenyl groups for use herein include, by way of example, a substituted or unsubstituted cyclic ring-containing radical containing from about 3 to about 30 carbon atoms with at least one carbon-carbon double bond such as, for example, cyclopropenyl, cyclobutenyl, cyclopentenyl and the like, wherein the cyclic ring can optionally contain one or more heteroatoms, e.g., O and N, and the like.

Representative examples of aryl groups for use herein include, by way of example, a substituted or unsubstituted monoaromatic or polyaromatic radical containing from about 5 to about 30 carbon atoms such as, for example, phenyl, naphthyl, tetrahydronapthyl, indenyl, biphenyl and the like, optionally containing one or more heteroatoms, e.g., O and N, and the like.

Representative examples of arylalkyl groups for use herein include, by way of example, a substituted or unsubstituted aryl group as defined herein directly bonded to an alkyl group as defined herein, e.g., —$CH_2C_6H_5$, —$C_2H_5C_6H_5$ and the like, wherein the aryl group can optionally contain one or more heteroatoms, e.g., O and N, and the like.

Representative examples of fluoroaryl groups for use herein include, by way of example, an aryl group as defined herein having one or more fluorine atoms attached to the aryl group.

Representative examples of ester groups for use herein include, by way of example, a carboxylic acid ester having one to 20 carbon atoms and the like.

Representative examples of ether or polyether containing groups for use herein include, by way of example, an alkyl ether, cycloalkyl ether, cycloalkylalkyl ether, cycloalkenyl ether, aryl ether, arylalkyl ether wherein the alkyl, cycloalkyl, cycloalkylalkyl, cycloalkenyl, aryl, and arylalkyl groups are as defined herein. Exemplary ether or polyether-containing groups include, by way of example, alkylene oxides, poly(alkylene oxide)s such as ethylene oxide, propylene oxide, butylene oxide, poly(ethylene oxide)s, poly(ethylene glycol)s, poly(propylene oxide)s, poly(butylene oxide)s and mixtures or copolymers thereof, an ether or polyether group of the general formula —$(R^2OR^3)_t$, wherein $R^2$ is a bond, a substituted or unsubstituted alkyl, cycloalkyl or aryl group as defined herein and $R^3$ is a substituted or unsubstituted alkyl, cycloalkyl or aryl group as defined herein and t is at least 1, e.g., —$CH_2CH_2OC_6H_5$ and $CH_2$—$CH_2$—$CH_2$—O—$CH_2$—$(CF_2)_z$—H where z is 1 to 6, —$CH_2CH_2OC_2H_5$, and the like.

Representative examples of alkyl or arylamide groups for use herein include, by way of example, an amide of the general formula —$R^4C(O)NR^5R^6$ wherein $R^4$, $R^5$ and $R^6$ are independently $C_1$-$C_{30}$ hydrocarbons, e.g., $R^4$ can be alkylene groups, arylene groups, cycloalkylene groups and $R^5$ and $R^6$ can be alkyl groups, aryl groups, and cycloalkyl groups as defined herein and the like.

Representative examples of alky or arylamine groups for use herein include, by way of example, an amine of the general formula —$R^7NR^8R^9$ wherein $R^7$ is a $C_2$-$C_{30}$ alkylene, arylene, or cycloalkylene and $R^8$ and $R^9$ are independently $C_1$-$C_{30}$ hydrocarbons such as, for example, alkyl groups, aryl groups, or cycloalkyl groups as defined herein.

Representative examples of alkoxy groups for use herein include, by way of example, an alkyl group as defined herein attached via oxygen linkage to the rest of the molecule, i.e., of the general formula —$OR^{10}$, wherein $R^{10}$ is an alkyl, cycloalkyl, cycloalkylalkyl, cycloalkenyl, aryl or an arylalkyl as defined herein, e.g., —$OCH_3$, —$OC_2H_5$, or —$OC_6H_5$, and the like.

Representative examples of heterocyclic ring groups for use herein include, by way of example, a substituted or unsubstituted stable 3 to about 30 membered ring radical, containing carbon atoms and from one to five heteroatoms, e.g., nitrogen, phosphorus, oxygen, sulfur and mixtures thereof. Suitable heterocyclic ring radicals for use herein may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heteroaromatic or heteroaryl aromatic). Examples of such heterocyclic ring radicals include, but are not limited to, azetidinyl, acridinyl, benzodioxolyl, benzodioxanyl, benzofurnyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroquinolinyl, tetrahydroisoquinolinyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxazolidinyl, triazolyl, indanyl, isoxazolyl, iso-oxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl, isochromanyl and the like and mixtures thereof.

Representative examples of heteroaryl groups for use herein include, by way of example, a substituted or unsubstituted heterocyclic ring radical as defined herein. The heteroaryl ring radical may be attached to the main structure at any heteroatom or carbon atom that results in the creation of a stable structure.

Representative examples of heteroarylalkyl groups for use herein include, by way of example, a substituted or unsubstituted heteroaryl ring radical as defined herein directly bonded to an alkyl group as defined herein. The heteroarylalkyl radical may be attached to the main structure at any carbon atom from the alkyl group that results in the creation of a stable structure.

Representative examples of heterocyclic groups for use herein include, by way of example, a substituted or unsubstituted heterocylic ring radical as defined herein. The heterocyclic ring radical may be attached to the main structure at any heteroatom or carbon atom that results in the creation of a stable structure.

Representative examples of heterocycloalkyl groups for use herein include, by way of example, a substituted or unsubstituted heterocylic ring radical as defined herein directly bonded to an alkyl group as defined herein. The heterocycloalkyl radical may be attached to the main structure at carbon atom in the alkyl group that results in the creation of a stable structure.

The substituents in the 'substituted alkyl', 'substituted alkoxy', 'substituted cycloalkyl', 'substituted cycloalkylalkyl', 'substituted cycloalkenyl', 'substituted arylalkyl', 'substituted aryl', 'substituted heterocyclic ring', 'substituted heteroaryl ring,' 'substituted heteroarylalkyl', 'substituted heterocycloalkyl ring', 'substituted cyclic ring', 'substituted carboxylic acid derivative', substituted alkylene, substituted disubstituted-arylene, substituted alkylene arylene, substituted arylene alkylene, substituted alkylene aryl alkylene, substituted cycloalkylene, substituted alkylene cycloalkyl, substituted cycloalkyl alkylene and substituted alkylene cycloalkyl alkylene may be the same or different and include one or more substituents such as hydrogen, hydroxy, halogen, carboxyl, cyano, nitro, oxo (=O), thio(=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocycloalkyl ring, substituted or unsubstituted heteroarylalkyl, substituted or unsubstituted heterocyclic ring, substituted or unsubstituted guanidine, —$COOR_x$, —$C(O)R_x$, —$C(S)R_x$, —$C(O)NR_xR_y$, —$C(O)ONR_xR_y$, —$NR_xCON-R_yR_z$, —$N(R_x)SOR_y$, —$N(R_x)SO_2R_y$, —(=N—N(Rx)R_y), —$NR_xC(O)OR_y$, —$NR_xR_y$, —$NR_xC(O)R_y$—, —$NR_xC(S)R_y$—$NR_xC(S)NR_yR_z$, —$SONR_xR_y$—, —$SO_2NR_xR_y$—, —$OR_x$, —$OR_xC(O)NR_yR_z$, —$OR_xC(O)OR_y$—, —$OC(O)R_x$, —$OC(O)NR_xR_y$, —$R_xNR_yC(O)R_z$, —$R_xOR_y$, —$R_xC(O)OR_y$, —$R_xC(O)NR_yR_z$, —$R_xC(O)R_x$, —$R_xOC(O)R_y$, —$SR_x$, —$SOR_x$, —$SO_2R_x$, —$ONO_2$, wherein $R_x$, $R_y$ and $R_z$ in each of the above groups can be the same or different and can be a hydrogen atom, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, 'substituted heterocycloalkyl ring' substituted or unsubstituted heteroarylalkyl, or a substituted or unsubstituted heterocyclic ring.

In general, a multi-armed macromonomer of the present invention can be obtained by linking the substantially linear arms, or "prearms" since they are not yet connected to the core, to the siloxy-containing core. In one embodiment, the substantially linear prearms of the multi-armed macromonomer of the present invention are represented by the structure of Formulae II or III:

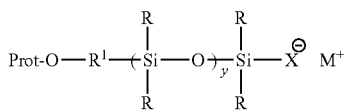

(II)

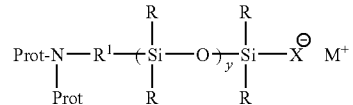

(III)

wherein y, R and X have the aforestated meanings; M is an alkali metal such as, for example, sodium, potassium, cesium, and lithium, $R^1$ is independently a bond, a substituted or unsubstituted divalent hydrocarbon radical having 1 to 30 carbon atoms which may include ether linkages therebetween including, by way of example, a substituted or unsubstituted $C_1$-$C_{30}$ alkylene, substituted or unsubstituted $C_3$-$C_{30}$ cycloalkylene, and substituted or unsubstituted $C_5$-$C_{30}$ arylene radical, substituted radicals of the foregoing in which some of the hydrogen atoms are substituted with halogen atoms, and combinations thereof as defined herein and Prot is independently a protecting group. Useful protecting groups include those represented by the formula —$Si(R^{15})(R^{16})(R^{17})$, wherein $R^{15}$, $R^{16}$ and $R^{17}$ are independently a straight or branched alkyl or aryl group having from 1 to about 25 carbon atoms as defined herein.

The macromonomer prearms of the present invention can be prepared by conventional techniques known in the art. For example, in one embodiment, macromonomer prearms of the present invention can be prepared according to the method generally shown in Scheme I below.

SCHEME I

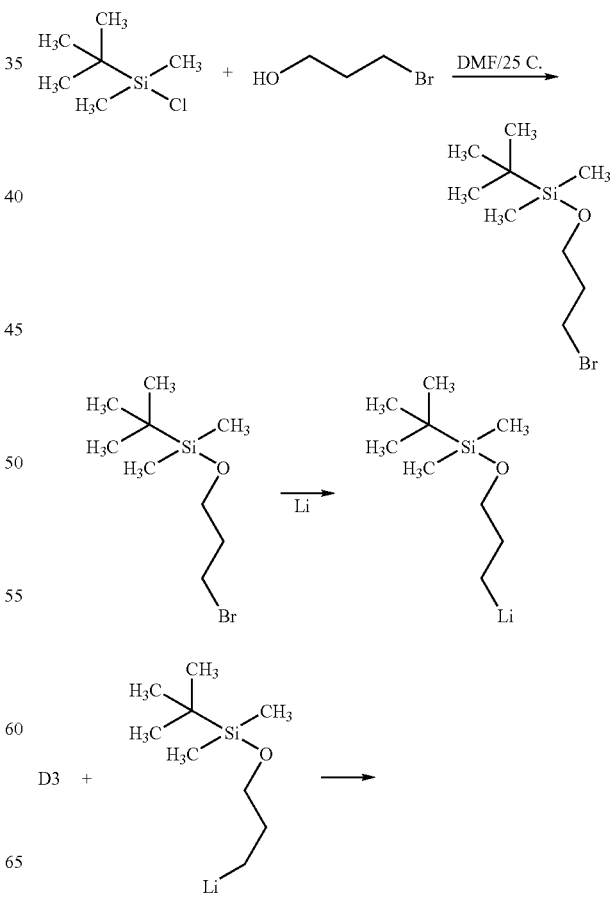

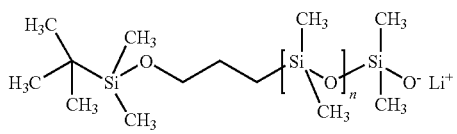

wherein D3 is hexamethylcyclotrisiloxane.

In another embodiment, macromonomer prearms of the present invention can be prepared according to the method generally shown in Scheme II below.

SCHEME II

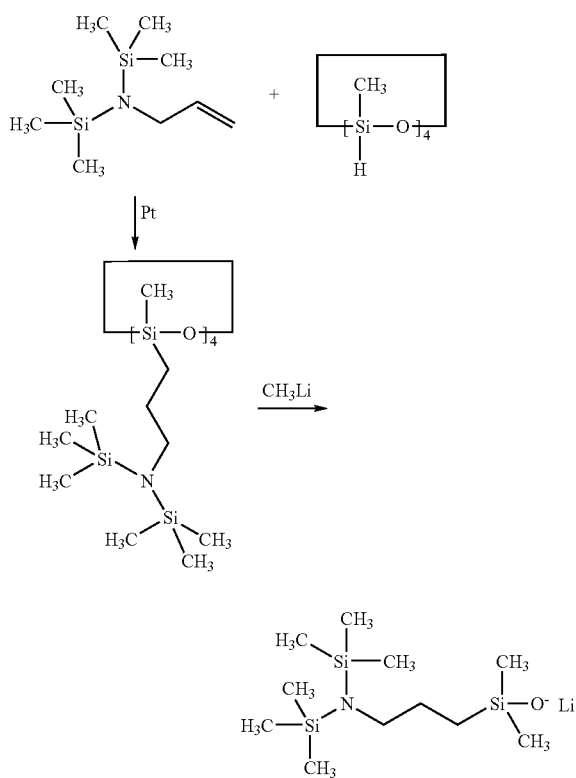

The macromonomer prearms such as those represented by general Formula II or III are linked with a siloxy- or polysiloxy-containing core reactant having reactive functionalities capable of linking the macromonomer prearms to the core reactant. In one embodiment, a suitable siloxy- or polysiloxy-containing core reactant for use herein is of general Formula IV:

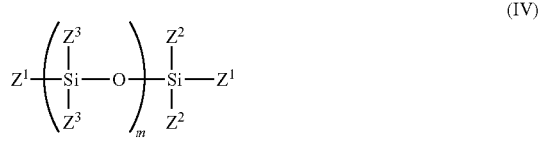

(IV)

wherein m has the aforestated meanings, $Z^1$ is independently a reactive functionality capable of linking the macromonomer prearms to the core reactant such as a halogen, e.g., Cl, and $Z^2$ and $Z^3$ are independently hydrogen, a straight or branched, substituted or unsubstituted $C_1$-$C_{30}$ alkyl group, a substituted or unsubstituted $C_3$-$C_{30}$ cycloalkyl group, a substituted or unsubstituted $C_3$-$C_{30}$ cycloalkylalkyl group, a substituted or unsubstituted $C_3$-$C_{30}$ cycloalkenyl group, a substituted or unsubstituted $C_5$-$C_{30}$ aryl group, and a substituted or unsubstituted $C_5$-$C_{30}$ arylalkyl group, a $C_1$-$C_{30}$ fluoro-substituted alkyl group or alkenyl group; a $C_1$-$C_{20}$ ester group; an ether or polyether-containing group; an alkyl- or arylamide group; an alkyl- or arylamine group; a substituted or unsubstituted $C_1$-$C_{30}$ alkoxy group; a substituted or unsubstituted $C_5$-$C_{30}$ heteroaryl group; a substituted or unsubstituted $C_3$-$C_{30}$ heterocyclic ring; a substituted or unsubstituted $C_4$-$C_{30}$ heterocycloalkyl group; a substituted or unsubstituted $C_6$-$C_{30}$ heteroarylalkyl group; a vinyl group; a $C_5$-$C_{30}$ fluoroalkyl or fluoroaryl group and combinations thereof and further wherein at least one of $Z^2$ and at least one of $Z^3$ in each repeating unit are independently a reactive functionality capable of linking the macromonomer prearms to the core reactant such as a halogen, e.g., Cl. The preparation of a polysiloxy-containing core reactant of Formula IV is within the purview of one skilled in the art and as exemplified in the examples.

When linking the foregoing macromonomer prearms to the siloxy- or polysiloxy-containing core reactant, any reaction vessel conventional in the art may be employed. Preferably, glass vessels should be presilylated with a chlorosilane or alkoxy silane to prevent diminution of the reactive silane core. The reaction vessel may be charged with the reaction mixture comprising the siloxy- or polysiloxy-containing core reactant and macromonomer prearm. In one embodiment, the siloxy- or polysiloxy-containing core reactant is first added, followed by slow addition of the macromonomer prearm with stirring. All conditions may be dry, and the reaction is performed under nitrogen or argon. In one embodiment, the reaction may be conducted at a temperature from about −15° C. to about 40° C. and preferably from about −5° C. to about 25° C. for a time period ranging from about 1 hour to about 8 hours. Additionally, the reaction may occur at atmospheric pressure; however, the pressure may be increased if desired, and substantially inert organic solvents like toluene or tetrahydrofuran may also be used to enhance the reaction conditions.

Generally, the siloxy- or polysiloxy-containing core reactant will be reacted with the macromonomer prearm in an excess amount in order to consume all of the prearm. Such amounts can be readily determined by one skilled in the art. Once the macromonomer prearms are linked to the core, the prearms are deprotected and then reacted with an ethylenically unsaturated containing radical to form the multi armed macromonomers of the present invention.

In another embodiment, a multi-armed macromonomer of the present invention can be obtained as follows. First, a hydrosilation reaction of a protected amine with a hydride containing cyclic siloxane using a suitable platinum catalyst such as a platinum divinyl complex commercially available from such sources as Aldrich Chemical Company (Milwaukee, Wis.). Next, the protected amine is lithiated with an alkyl lithium to form a protected amine lithium silanolate initiating species. Third, an anionic ring opening polymerization reaction of a commercially available hexamethylcyclotrisiloxane (D3) in a nonpolar solvent such as an aromatic hydrocarbon, e.g., cyclohexane, or an aliphatic hydrocarbon, e.g., hexane, at a temperature of between about 5° C. to about 60° C. for about 1 to about 4 hours followed by termination of the alkyldimethylsiloxanesilanolate anion with an excess of chlorosilane (e.g., about 1.1 to 5 times the amount of alkyllithium reagent used). To obtain a narrow dispersity, the ring opening reaction can be conducted in a polar chain propagating aprotic solvent such as tetrahydrofuran until complete conversion of D3 is observed by gas chromatography analysis. The resulting reaction product is purified by filtration of LiCl, excess chlorodimethylsilane is evaporated, followed by deprotection of the amine group with an alcohol. The resultant amine-terminated multifunctional siloxane is washed with an aqueous base (e.g., dilute sodium bicarbonate) and dried using, for example, anhydrous sodium sulfate, followed by thin film purification to remove water and any residual traces of D3, higher cyclics and any other volatiles. The final step involves methacrylation using an excess of methacryloyl chloride using an amine scavenger and again washing and thin film evaporation. An illustrative scheme of this synthesis is generally depicted in Schemes III and IV below:

SCHEME III

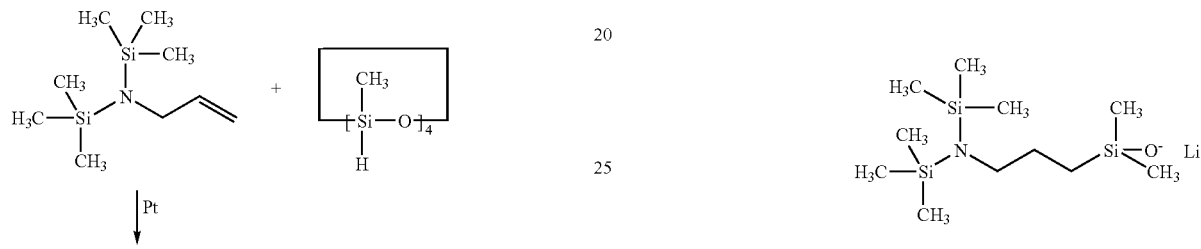

SCHEME IV

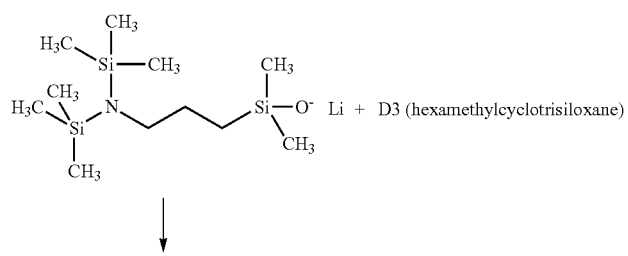

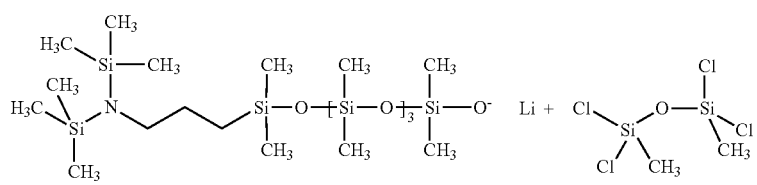

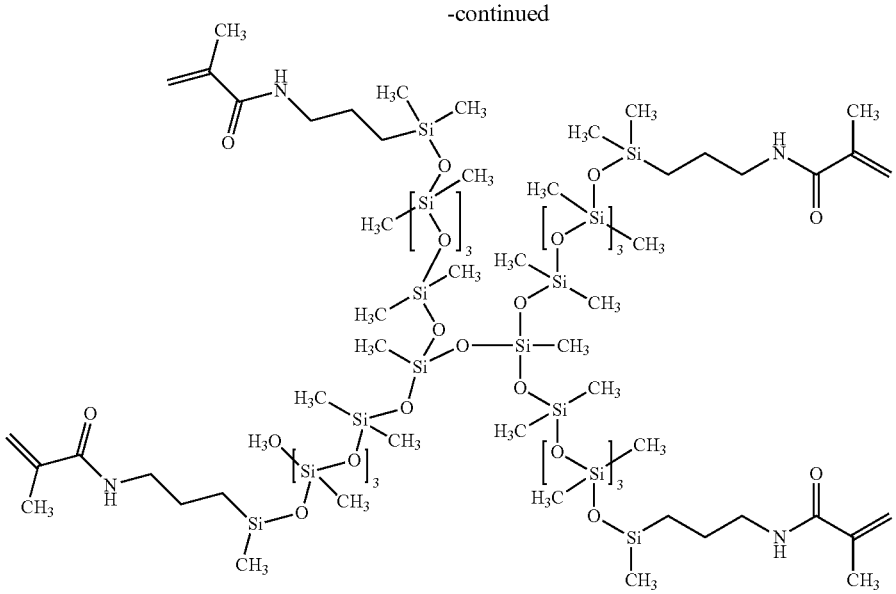

As one skilled in the art will readily appreciate, the number of arms which can be linked will depend on the structure of the siloxy- or polysiloxy-containing core reactant. For example, with a reactive chlorosiloxy- or polysiloxy-containing core, the number of arms which can be linked is believed to substantially equate to the number of Si—Cl groups available in the siloxy- or polysiloxy-containing core reactant. Theoretically, the number of arms present in the multi-armed macromonomers of the present invention can range from 4 to about 100. Accordingly, the structure of the resultant multi-armed macromonomers is therefore dependent on the structure of the siloxy- or polysiloxy-containing core reactant.

Another embodiment of the present invention provides a polymeric material comprising a polymerization product of a monomeric mixture containing at least a multi-armed macromonomer disclosed herein and one or more comonomers. Since the macromonomers are endcapped with a polymerizable ethylenically unsaturated-containing radical, they are polymerizable by free radical polymerization. The one or more comonomers employed in the monomeric mixtures include conventional biomedical device-forming or lens-forming monomers. As used herein, the term "monomer" or "monomeric" and like terms denote relatively low molecular weight compounds that are polymerizable by free radical polymerization, as well as higher molecular weight compounds also referred to as "prepolymers", "macromonomers", and related terms. Generally, the biomedical device-forming comonomer contains at least one polymerizable group. In one embodiment, a suitable comonomer includes hydrophobic monomers, hydrophilic monomers and the like and mixtures thereof.

Representative examples of hydrophilic comonomers include, but are not limited to, unsaturated carboxylic acids, such as methacrylic and acrylic acids; (meth)acrylic substituted alcohols or polyols such as 2-hydroxyethyl methacrylate, 2-hydroxyethyl acrylate, glyceryl methacrylate and the like; vinyl lactams such as N-vinylpyrrolidone and the like; and (meth)acrylamides such as methacrylamide, N,N-dimethylacrylamide and the like and combinations thereof. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the art. The hydrophilic monomers can be present in the monomeric mixtures in an amount ranging from 0 to about 70 weight percent, based on the total weight of the mixture.

According to various preferred embodiments, the initial monomeric mixture can comprise at least one (meth)acrylic substituted alcohol, such as at least one of 2-hydroxyethyl methacrylate and glyceryl methacrylate, preferably in an amount of at least about 1 weight percent of the monomeric mixture, and preferably in an amount of about 2 to about 40 weight percent. Preferably, the monomeric mixture further includes at least one vinyl lactam, such as N-vinylpyrrolidone and/or at least one (meth)acrylamide, such as N,N-dimethylacrylamide.

Suitable hydrophobic monomers include $C_1$-$C_{20}$ alkyl and $C_3$-$C_{20}$ cycloalkyl(meth)acrylates, substituted and unsubstituted $C_6$-$C_{30}$ aryl(meth)acrylates, (meth)acrylonitriles, fluorinated alkyl methacrylates, long-chain acrylamides such as octyl acrylamide, and the like. The hydrophobic monomers can be present in the monomeric mixtures in an amount ranging from 0 to about 30 weight percent, based on the total weight of the mixture.

Another class of device-forming or lens-forming monomers is silicone-containing monomers. In other words, another silicone-containing comonomer which contains from 1 to about 60 silicone atoms, in addition to the multi-armed macromonomer of this invention, may be included in the initial monomeric mixture, for example, if it is desired to obtain a copolymer with high oxygen permeability. Applicable silicone-containing monomers for use in the formation of contact lenses such as silicone hydrogels are well known in the art and numerous examples are provided in, for example, U.S. Pat. Nos. 4,136,250; 4,153,641; 4,740,533; 5,034,461; 5,070,215; 5,260,000; 5,310,779; and 5,358,995.

Representative examples of applicable silicon-containing monomers include bulky polysiloxanylalkyl(meth)acrylic monomers. An example of a bulky polysiloxanylalkyl(meth) acrylic monomer is represented by the structure of Formula V:

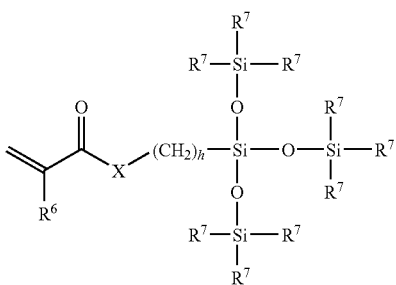
(V)

wherein X denotes —O— or —NR— wherein R denotes hydrogen or a $C_1$-$C_4$ alkyl; each $R^6$ independently denotes hydrogen or methyl; each $R^7$ independently denotes a lower alkyl radical, phenyl radical or a group represented by

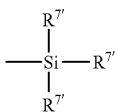

wherein each $R^{7'}$ independently denotes a lower alkyl or phenyl radical; and h is 1 to 10.

Representative examples of other applicable silicon-containing monomers includes, but are not limited to, bulky polysiloxanylalkyl carbamate monomers as generally depicted in Formula Va:

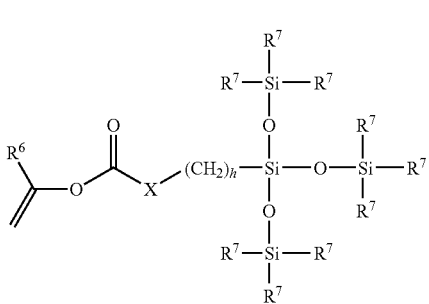
(Va)

wherein X denotes —NR—; wherein R denotes hydrogen or a $C_1$-$C_4$ alkyl; $R^6$ denotes hydrogen or methyl; each $R^7$ independently denotes a lower alkyl radical, phenyl radical or a group represented by

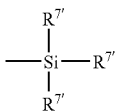

wherein each $R^{7'}$ independently denotes a lower alkyl or phenyl radical; and h is 1 to 10, and the like.

Examples of bulky monomers are 3-methacryloyloxypropyltris(trimethylsiloxy)silane or tris(trimethylsiloxy)silylpropyl methacrylate, sometimes referred to as TRIS and tris (trimethylsiloxy)silylpropyl vinyl carbamate, sometimes referred to as TRIS-VC and the like and mixtures thereof.

Such bulky monomers may be copolymerized with a silicone macromonomer, which is a poly(organosiloxane) capped with an unsaturated group at two or more ends of the molecule. U.S. Pat. No. 4,153,641 discloses, for example, various unsaturated groups such as acryloxy or methacryloxy groups.

Another class of representative silicone-containing monomers includes, but is not limited to, silicone-containing vinyl carbonate or vinyl carbamate monomers such as, for example, 1,3-bis[4-vinyloxycarbonyloxy)but-1-yl]tetramethyldisiloxane; 3-(trimethylsilyl)propyl vinyl carbonate; 3-(vinyloxycarbonylthio)propyl-[tris(trimethylsiloxy)silane]; 3-[tris(trimethylsiloxy)silyl]propyl vinyl carbamate; 3-[tris(trimethylsiloxy)silyl]propyl allyl carbamate; 3-[tris(trimethylsiloxy)silyl]propyl vinyl carbonate; t-butyldimethylsiloxyethyl vinyl carbonate; trimethylsilylethyl vinyl carbonate; trimethylsilylmethyl vinyl carbonate and the like.

Another class of silicon-containing monomers includes polyurethane-polysiloxane macromonomers (also sometimes referred to as prepolymers), which may have hard-soft-hard blocks like traditional urethane elastomers. Examples of silicone urethanes are disclosed in a variety or publications, including Lai, Yu-Chin, "The Role of Bulky Polysiloxanylalkyl Methacryates in Polyurethane-Polysiloxane Hydrogels," Journal of Applied Polymer Science, Vol. 60, 1193-1199 (1996). PCT Published Application No. WO 96/31792 also discloses examples of such monomers, the contents of which are hereby incorporated by reference in its entirety. Further examples of silicone urethane monomers are represented by Formulae VI and VII:

$$E(*D*A*D*G)_a*D*A*D*E'; \text{ or} \qquad (VI)$$

$$E(*D*G*D*A)_a*D*A*D*E'; \text{ or} \qquad (VII)$$

wherein:

D denotes an alkyl diradical, an alkyl cycloalkyl diradical, a cycloalkyl diradical, an aryl diradical or an alkylaryl diradical having 6 to about 30 carbon atoms;

G denotes an alkyl diradical, a cycloalkyl diradical, an alkyl cycloalkyl diradical, an aryl diradical or an alkylaryl diradical having 1 to about 40 carbon atoms and which may contain ether, thio or amine linkages in the main chain;

* denotes a urethane or ureido linkage;

a is at least 1;

A denotes a divalent polymeric radical of Formula VIII:

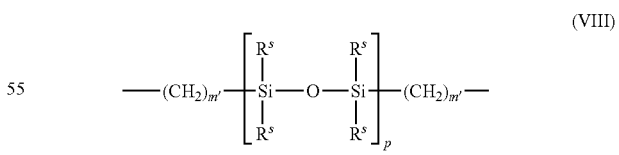
(VIII)

wherein each $R^s$ independently denotes an alkyl or fluoro-substituted alkyl group having 1 to about 10 carbon atoms which may contain ether linkages between the carbon atoms; m' is at least 1; and p is a number that provides a moiety weight of about 400 to about 10,000;

each of E and E' independently denotes a polymerizable unsaturated organic radical represented by Formula IX:

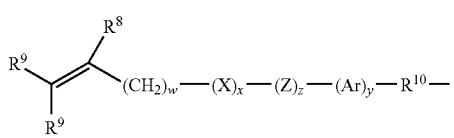

(IX)

wherein: $R^8$ is hydrogen or methyl;
$R^9$ is independently hydrogen, an alkyl radical having 1 to 6 carbon atoms, or a —CO—Y—$R^{11}$ radical wherein Y is —O—, —S— or —NH—;
$R^{10}$ is a divalent alkylene radical having 1 to about 10 carbon atoms;
$R^{11}$ is a alkyl radical having 1 to about 12 carbon atoms;
X denotes —CO— or —OCO—;
Z denotes —O— or —NH—;
Ar denotes an aromatic radical having about 6 to about 30 carbon atoms;
w is 0 to 6; x is 0 or 1; y is 0 or 1; and z is 0 or 1.

A preferred silicone-containing urethane monomer is represented by Formula X:

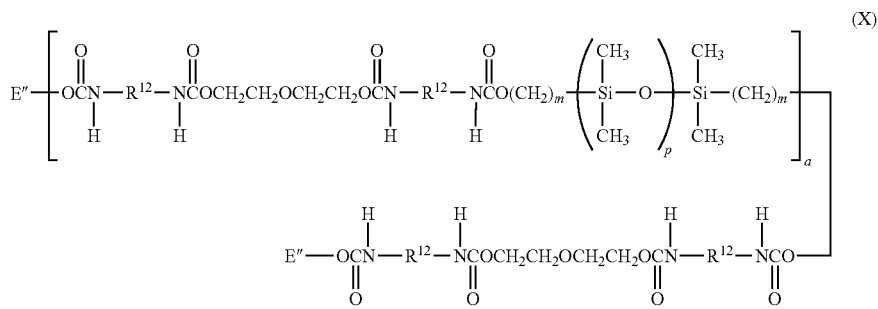

(X)

wherein m is at least 1 and is preferably 3 or 4, a is at least 1 and preferably is 1, p is a number which provides a moiety weight of about 400 to about 10,000 and is preferably at least about 30, $R^{12}$ is a diradical of a diisocyanate after removal of the isocyanate group, such as the diradical of isophorone diisocyanate, and each E" is a group represented by:

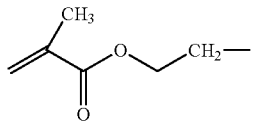

Another class of representative silicone-containing monomers includes fluorinated monomers. Such monomers have been used in the formation of fluorosilicone hydrogels to reduce the accumulation of deposits on contact lenses made therefrom, as described in, for example, U.S. Pat. Nos. 4,954,587; 5,010,141 and 5,079,319. The use of silicone-containing monomers having certain fluorinated side groups, i.e., —($CF_2$)—H, have been found to improve compatibility between the hydrophilic and silicone-containing monomeric units, see, e.g., U.S. Pat. Nos. 5,321,108 and 5,387,662.

The above silicone materials are merely exemplary, and other materials for use in forming biomedical devices according to the present invention and have been disclosed in various publications and are being continuously developed for use in contact lenses and other biomedical devices can also be used.

For example, a biomedical device-forming comonomer can be a cationic monomer such as cationic silicone-containing monomer or cationic fluorinated silicone-containing monomers.

The monomer mixtures may include the silicone comonomer, in addition to the subject multi-armed macromonomers, at 0 to about 50 weight percent, preferably about 5 to about 30 weight percent when present.

In one embodiment, the monomer mixture can contain a multi-armed macromonomer of the present invention and one or more of the foregoing silicone-containing monomers and one or more of the foregoing hydrophilic monomers and/or hydrophobic monomers.

The monomer mixture can also include a crosslinking monomer (a crosslinking monomer being defined as a monomer having multiple polymerizable functionalities). Since the multi-armed macromonomer of this invention are endcapped with a polymerizable ethylenically unsaturated-containing radical, the multi-armed polysiloxane macromonomers can function as a crosslinker. Optionally, a supplemental crosslinking monomer may be added to the initial monomeric mixture. Representative crosslinking monomers include: divinylbenzene, allyl methacrylate, ethyleneglycol dimethacrylate, tetraethyleneglycol dimethacrylate, polyethyleneglycol dimethacrylate, vinyl carbonate derivatives of the glycol dimethacrylates, and methacryloxyethyl vinylcarbonate. When a supplemental crosslinking agent is employed, this monomeric material may be included in the monomer mixture at about 0.1 to about 20 weight percent, and more preferably at about 0.2 to about 10 weight percent.

Although not required, homopolymers or copolymers within the scope of the present invention may optionally have one or more strengthening agents added prior to polymerization, preferably in quantities of less than about 80 weight percent and preferably from about 20 to about 60 weight percent. Non-limiting examples of suitable strengthening agents are described in U.S. Pat. Nos. 4,327,203; 4,355,147; and 5,270,418; each of which is incorporated herein in its entirety by reference. Specific examples, not intended to be limiting, of such strengthening agents include cycloalkyl acrylates and methacrylates; e.g., tert-butylcyclohexyl methacrylate and isopropylcyclopentyl acrylate.

The monomeric mixture may further contain, as necessary and within limits not to impair the purpose and effect of the present invention, various additives such as an antioxidant, coloring agent, ultraviolet absorber, lubricant internal wetting agents, toughening agents and the like and other constituents as is well known in the art.

The biomedical devices of the present invention, e.g., contact lenses or intraocular lenses, can be prepared by polymerizing the foregoing monomeric mixtures to form a product that can be subsequently formed into the appropriate shape by, for example, lathing, injection molding, compression molding, cutting and the like. For example, in producing contact lenses, the initial monomeric mixture may be polymerized in tubes to provide rod-shaped articles, which are then cut into buttons. The buttons may then be lathed into contact lenses.

Alternately, the biomedical devices such as contact lenses may be cast directly in molds, e.g., polypropylene molds, from the monomeric mixtures, e.g., by spincasting and static casting methods. Spincasting methods are disclosed in U.S. Pat. Nos. 3,408,429 and 3,660,545, and static casting methods are disclosed in U.S. Pat. Nos. 4,113,224, 4,197,266, and 5,271,875. Spincasting methods involve charging the monomer mixture to a mold, and spinning the mold in a controlled manner while exposing the monomer mixture to a radiation source such as UV light. Static casting methods involve charging the monomeric mixture between two mold sections, one mold section shaped to form the anterior lens surface and the other mold section shaped to form the posterior lens surface, and curing the monomeric mixture while retained in the mold assembly to form a lens, for example, by free radical polymerization of the monomeric mixture. Examples of free radical reaction techniques to cure the lens material include thermal radiation, infrared radiation, electron beam radiation, gamma radiation, ultraviolet (UV) radiation, and the like; or combinations of such techniques may be used. U.S. Pat. No. 5,271,875 describes a static cast molding method that permits molding of a finished lens in a mold cavity defined by a posterior mold and an anterior mold. As an additional method, U.S. Pat. No. 4,555,732 discloses a process where an excess of a monomeric mixture is cured by spincasting in a mold to form a shaped article having an anterior lens surface and a relatively large thickness, and the posterior surface of the cured spincast article is subsequently lathed to provide a contact lens having the desired thickness and posterior lens surface.

Polymerization may be facilitated by exposing the mixture to heat and/or radiation, such as ultraviolet light, visible light, or high energy radiation. A polymerization initiator may be included in the mixture to facilitate the polymerization step. Representative examples of free radical thermal polymerization initiators include organic peroxides such as acetyl peroxide, lauroyl peroxide, decanoyl peroxide, stearoyl peroxide, benzoyl peroxide, tertiarylbutyl peroxypivalate, peroxydicarbonate, and the like. Representative UV initiators are those known in the art and include benzoin methyl ether, benzoin ethyl ether, Darocure 1173, 1164, 2273, 1116, 2959, 3331 (EM Industries) and Igracure 651 and 184 (Ciba-Geigy), and the like. Generally, the initiator will be employed in the monomeric mixture at a concentration of about 0.01 to about 5 percent by weight of the total mixture.

Polymerization is generally performed in a reaction medium, such as, for example, a solution or dispersion using a solvent, e.g., water or an alkanol containing from 1 to 4 carbon atoms such as methanol, ethanol or propan-2-ol. Alternatively, a mixture of any of the above solvents may be used.

Generally, polymerization can be carried out for about 15 minutes to about 72 hours, and under an inert atmosphere of, for example, nitrogen or argon. If desired, the resulting polymerization product can be dried under vacuum, e.g., for about 5 to about 72 hours or left in an aqueous solution prior to use.

Polymerization of the mixtures will yield a polymer, that when hydrated, forms a hydrogel. Generally, the mixture will contain the multi-armed macromonomers of the present invention in an amount ranging from about 0.1 to about 50 weight percent, and preferably about 1 to about 25 weight percent, based on the total weight of the monomer mixture. The biomedical device-forming comonomer may be present in the mixture in an amount ranging from about 50 to about 99.9 weight percent, and preferably from about 75 to about 99 weight percent, based on the total weight of the mixture.

When producing a hydrogel lens, the mixture may further include at least a diluent that is ultimately replaced with water when the polymerization product is hydrated to form a hydrogel. Generally, the water content of the hydrogel is greater than about 5 weight percent and more commonly between about 10 to about 80 weight percent. The amount of diluent used should be less than about 50 weight percent and in most cases, the diluent content will be less than about 30 weight percent. However, in a particular polymer system, the actual limit will be dictated by the solubility of the various monomers in the diluent. In order to produce an optically clear copolymer, it is important that a phase separation leading to visual opacity does not occur between the comonomers and the diluent, or the diluent and the final copolymer.

Furthermore, the maximum amount of diluent which may be used will depend on the amount of swelling the diluent causes the final polymers. Excessive swelling will or may cause the copolymer to collapse when the diluent is replaced with water upon hydration. Suitable diluents include, but are not limited to, ethylene glycol; glycerine; liquid poly(ethylene glycol); alcohols; alcohol/water mixtures; ethylene oxide/propylene oxide block copolymers; low molecular weight linear poly(2-hydroxyethyl methacrylate); glycol esters of lactic acid; formamides; ketones; dialkylsulfoxides; butyl carbitol; and the like and mixtures thereof.

If necessary, it may be desirable to remove residual diluent from the lens before edge-finishing operations which can be accomplished by evaporation at or near ambient pressure or under vacuum. An elevated temperature can be employed to shorten the time necessary to evaporate the diluent. The time, temperature and pressure conditions for the solvent removal step will vary depending on such factors as the volatility of the diluent and the specific monomeric components, as can be readily determined by one skilled in the art. If desired, the mixture used to produce the hydrogel lens may further include crosslinking and wetting agents known in the prior art for making hydrogel materials.

In the case of intraocular lenses, the monomer mixtures may further include a monomer for increasing the refractive index of the resultant copolymer. Examples of such monomers are aromatic(meth)acrylates, such as phenyl(meth)acrylate, 2-phenylethyl(meth)acrylate, 2-phenoxyethyl methacrylate, and benzyl(meth)acrylate.

The biomedical devices such as contact lenses obtained herein may be subjected to optional machining operations. For example, the optional machining steps may include buffing or polishing a lens edge and/or surface. Generally, such machining processes may be performed before or after the product is released from a mold part, e.g., the lens is dry released from the mold by employing vacuum tweezers to lift the lens from the mold, after which the lens is transferred by means of mechanical tweezers to a second set of vacuum tweezers and placed against a rotating surface to smooth the surface or edges. The lens may then be turned over in order to machine the other side of the lens.

The lens may then be transferred to individual lens packages containing a buffered saline solution. The saline solution may be added to the package either before or after transfer of the lens. Appropriate packaging designs and materials are known in the art. A plastic package is releasably sealed with a film. Suitable sealing films are known in the art and include foils, polymer films and mixtures thereof. The sealed packages containing the lenses are then sterilized to ensure a sterile product. Suitable sterilization means and conditions are known in the art and include, for example, autoclaving.

As one skilled in the art will readily appreciate other steps may be included in the molding and packaging process described above. Such other steps can include, for example, coating the formed lens, surface treating the lens during formation (e.g., via mold transfer), inspecting the lens, discarding defective lenses, cleaning the mold halves, reusing the mold halves, and the like and combinations thereof.

The following examples are provided to enable one skilled in the art to practice the invention and are merely illustrative of the invention. The examples should not be read as limiting the scope of the invention as defined in the claims.

EXAMPLE 1

Preparation of 1,1,3,3-tetrachloro-1,3-dimethyldisiloxane.
To a round bottom flask equipped with a stirrer and containing dry diethylether and the acid scavenger triethylamine is added under dry nitrogen freshly distilled trichloromethylsilane. The reaction mixture is cooled to 0° C. at which time is slowly added one equivalent of distilled water. The reaction is brought to room temperature and allowed to stir for an additional hour at which time the reaction mixture is filtered and rotory evaporated to remove the solvent. The resultant oil is fractionally distilled to give the desired product. This reaction is illustrated as follows:

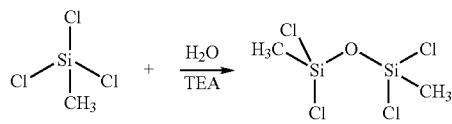

EXAMPLE 2

Preparation of 1,3,5,7-tetrakis[N,N-bis(trimethylsilyl)aminopropyl]-1,3,5,7-tetramethylcyclotetrasiloxane (TSS).
To a round bottom flask equipped with drying tube and stirrer is added N,N-bis(trimethylsilyl)allylamine with a catalytic amount of a platinum divinyl complex (commercially available from Aldrich Chemical Company) to which is added D4' (1,3,5,7-tetramethylcyclotetracyclotetrasiloxane) and heated to 100° C. The mixture is stirred for eight hours and the contents are vacuum distilled to give the desired product in high yield (TSS).

EXAMPLE 3

Preparation of N,N-bis(trimethylsilyl)aminopropyl-terminated multifunctional siloxane (AMS).
The TSS (0.96 mole) of Example 2 is added to tetrahydrofuran (THF) at room temperature containing methyl lithium (3.84 mole). The reaction mixture is stirred for two hours at which time is slowly added freshly sublimed hexamethylcyclotrisiloxane in a dry THF solution. The reaction mixture is heated to 55° C. and after two hours freshly distilled 1,1,3,3-tetrachloro-1,3-dimethyldisiloxane of Example 1 is added. The reaction mixture is stirred for one hour resulting in a multifunctional trimethylsilyl amine protected monodispersed siloxane. The amine protecting group is removed simply by heating the reaction mixture in ethanol to provide AMS. The deprotected multifunctional siloxane is devolatilized using a thin-film evaporator to remove solvent and other impurities.

EXAMPLE 4

Preparation of methacrylamide terminated multifunctional siloxane (MTS).
The deprotected multifunctional siloxane (AMS) of Example 3 is added to a solution of dry diethyl ether and the acid scavenger triethylamine. The reaction mixture is cooled to 5° C. and methacryloyl chloride is slowly added. The mixture is brought to room temperature and allowed to stir overnight at which time the mixture is washed 1× with dilute acid, 1× time with sodium bicarbonate and 1× with distilled water. The ether layer is collected and dried over magnesium sulfate and the ether is removed by rotoevaporator resulting in a methacrylamide terminated multifunctional siloxane (MTS).

EXAMPLE 5

Preparation of Films from the MTS of Example 4.
MTS of Example 4 and $M_2D_{25}$ as prepared in U.S. Pat. No. 6,762,264 are dissolved in a solvent, such as hexanol, at a desired ratio, along with a minor amount of Darocur-1173 initiator. The mixture is cast between silane-treated glass plates by curing under UV light.

EXAMPLE 6

Preparation of Films from the MTS of Example 4.
MTS of Example 4 and methyl methacrylate are dissolved in a solvent, at a desired ratio, along with a minor amount of Darocur-1173 initiator. The mixture is cast between silane-treated glass plates by curing under UV light.

EXAMPLE 7

Preparation of Films from the MTS of Example 4.
MTS of Example 4, methacryloxypropyl tris(trimethylsiloxy)silane (TRIS) and N,N-dimethylacrylamide (DMA) are dissolved in a solvent, at a desired ratio, along with a minor amount of Darocur-1173 initiator. The mixture is cast between silane-treated glass plates by curing under UV light.

EXAMPLE 8

Preparation of Films from the MTS of Example 4.
MTS of Example 4, TRIS, DMA, N-vinyl pyrrolidone (NVP) are dissolved in a solvent, at a desired ratio, along with a minor amount of Darocur-1173 initiator. The mixture is cast between silane-treated glass plates by curing under UV light.

EXAMPLE 9

Preparation of Films from the MTS of Example 4.
MTS of Example 4, DMA and NVP are dissolved in a solvent, at a desired ratio, along with a minor amount of Darocur-1173 initiator. The mixture is cast between silane-treated glass plates by curing under UV light.

EXAMPLE 10

Preparation of Films from the MTS of Example 4.
MTS of Example 4, tris(trimethylsiloxy)silylpropyl vinyl carbamate (TRIS-VC) and DMA are dissolved in a solvent, at a desired ratio, along with a minor amount of Darocur-1173 initiator. The mixture is cast between silane-treated glass plates by curing under UV light.

EXAMPLE 11

Preparation of Films from the MTS of Example 4.

MTS of Example 4, TRIS-VC, DMA and NVP are dissolved in a solvent, at a desired ratio, along with a minor amount of Darocur-1173 initiator. The mixture is cast between silane-treated glass plates by curing under UV light.

EXAMPLE 12

Preparation of Films from the MTS of Example 4.

MTS of Example 4, TRIS-dimer and DMA are dissolved in a solvent, at a desired ratio, along with a minor amount of Darocur-1173 initiator. The mixture is cast between silane-treated glass plates by curing under UV light.

EXAMPLE 13

Preparation of Films from the MTS of Example 4.

MTS of Example 4, TRIS-dimer, DMA and NVP are dissolved in a solvent, at a desired ratio, along with a minor amount of Darocur-1173 initiator. The mixture is cast between silane-treated glass plates by curing under UV light.

EXAMPLE 14

Preparation of Contact Lenses

A monomer mixture of Example 7 is injected onto a clean polypropylene anterior mold half, the molding surface of which is shaped to provide an anterior contact lens surface, and covered with the complementary polypropylene posterior mold half, the molding surface of which is shaped to provide a posterior contact lens surface. The mold halves are compressed, and the mixture is cured by exposure to UV radiation. The top mold half is removed, and the lens is removed from the bottom mold half. After extracting residuals from the lens, the lens is hydrated in buffered saline.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. A copolymer comprising a polymerization product of a monomeric mixture comprising one or more of multi-armed macromonomers comprising multiple side chains attached to a siloxy-containing core terminated on each end with one or more first substantially linear polysiloxane radicals having a polymerizable ethylenically unsaturated-containing terminal group, wherein each side chain comprises a second substantially linear polysiloxane radical having a polymerizable ethylenically unsaturated-containing terminal group.

2. The copolymer of claim 1, wherein the polymerizable groups of the first and second substantially linear polysiloxane radicals comprises a vinyl, allyl, vinyloxy, vinyl carbonate, vinyl carbamate, acryloyl, acryloyloxy, methacryloyl, methacryloyloxy, fumaryl, styryl, itaconyl, maleimido, methacrylamido or acrylamido-containing group.

3. The copolymer of claim 1, wherein the multi-armed macromonomer is of Formula I:

$$T^1-\left(\begin{array}{c}T^3\\|\\Si-O\\|\\T^3\end{array}\right)_m \begin{array}{c}T^2\\|\\Si-T^1\\|\\T^2\end{array} \quad (I)$$

wherein m is at least 1 and each $T^1$ is independently $$A-\begin{array}{c}R\\|\\Si\\|\\R\end{array}\!\!-\!\!\left(O-\begin{array}{c}R\\|\\Si\\|\\R\end{array}\right)_y\!\!-\!\!X-$$

wherein y is at least 1, R is independently a monovalent hydrocarbon radical having 1 to 30 carbon atoms which may include ether linkages therebetween, a halogen substituted monovalent hydrocarbon radical having 1 to about 20 carbon atoms which may include ether linkages therebetween, a $C_1$-$C_{20}$ ester group, an ether or polyether-containing group, an alkyl- or arylamide group, an alkyl- or arylamine group, a substituted or unsubstituted $C_1$-$C_{30}$ alkoxy group and combinations thereof, X is —O—, and A is independently a polymerizable ethylenically unsaturated-containing radical and $T^2$ and $T^3$ are independently hydrogen, a straight or branched, substituted or unsubstituted $C_1$-$C_{30}$ alkyl group, a substituted or unsubstituted $C_3$-$C_{30}$ cycloalkyl group, a substituted or unsubstituted $C_3$-$C_{30}$ cycloalkylalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ arylalkyl group, a $C_1$-$C_{30}$ fluoro-substituted alkyl group or alkenyl group, a $C_1$-$C_{20}$ ester group, an ether or polyether-containing group, an alkyl- or arylamide group, an alkyl- or arylamine group, a substituted or unsubstituted $C_1$-$C_{30}$ alkoxy group, a substituted or unsubstituted $C_5$-$C_{30}$ heteroaryl group, a substituted or unsubstituted $C_3$-$C_{30}$ heterocyclic ring, a substituted or unsubstituted $C_4$-$C_{30}$ heterocycloalkyl group, a substituted or unsubstituted $C_6$-$C_{30}$ heteroarylalkyl group, a vinyl group; a $C_5$-$C_{30}$ fluoroalkyl or fluoroaryl group and combinations thereof and further wherein at least one of $T^2$ and at least one of $T^3$ are independently of the same formula as $T^1$.

4. The copolymer of claim 1, wherein the monomeric mixture further comprises a hydrophilic monomer, hydrophobic monomer or both.

5. The copolymer of claim 4, wherein the hydrophilic monomer is selected from the group consisting of an unsaturated carboxylic acid, (meth)acrylic substituted alcohol, vinyl lactam, (meth)acrylamide and combinations thereof.

6. The copolymer of claim 1, wherein the monomeric mixture further comprises a hydrophilic monomer selected from the group consisting of 2-hydroxyethyl methacrylate, 2-hydroxyethyl acrylate, glyceryl methacrylate; N-vinylpyrrolidone; N-vinyl-N-methyl acetamide, N,N-dimethyl methacrylamide, N,N-dimethylacrylamide, acrylic acid, methacrylic acid and combinations thereof.

7. The copolymer of claim 4, wherein the hydrophobic monomer is a silicone-containing monomer having from 1 to about 20 silicon atoms.

8. The copolymer of claim 4, wherein the hydrophobic monomer is an aliphatic ring containing monomer selected from the group consisting of isobornyl acrylate, isobornyl methacrylate, cyclohexyl acrylate, cyclohexyl methacrylate and combinations thereof.

9. A biomedical device comprising a polymerization product of a monomeric mixture comprising (a) one or more of multi-armed macromonomers comprising multiple side chains attached to a siloxy-containing core terminated on each end with one or more first substantially linear polysiloxane radicals having a polymerizable ethylenically unsaturated-containing terminal group, wherein each side chain comprises a second substantially linear polysiloxane radical having a polymerizable ethylenically unsaturated-containing terminal group; and (b) a biomedical device-forming comonomer.

10. The biomedical device of claim 9, wherein the multi-armed macromonomer is of Formula I:

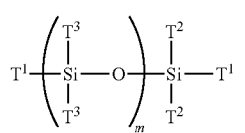

wherein m is at least 1 and each $T^1$ is independently

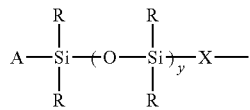

wherein y is at least 1, R is independently a monovalent hydrocarbon radical having 1 to 30 carbon atoms which may include ether linkages therebetween, a halogen substituted monovalent hydrocarbon radical having 1 to about 20 carbon atoms which may include ether linkages therebetween, a $C_1$-$C_{20}$ ester group, an ether or polyether-containing group, an alkyl- or arylamide group, an alkyl- or arylamine group, a substituted or unsubstituted $C_1$-$C_{30}$ alkoxy group and combinations thereof, X is —O—, and A is independently a polymerizable ethylenically unsaturated-containing radical and $T^2$ and $T^3$ are independently hydrogen, a straight or branched, substituted or unsubstituted $C_1$-$C_{30}$ alkyl group, a substituted or unsubstituted $C_3$-$C_{30}$ cycloalkyl group, a substituted or unsubstituted $C_3$-$C_{30}$ cycloalkylalkyl group, a substituted or unsubstituted $C_3$-$C_{30}$ cycloalkenyl group, a substituted or unsubstituted $C_5$-$C_{30}$ aryl group, a substituted or unsubstituted $C_5$-$C_{30}$ arylalkyl group, a $C_1$-$C_{30}$ fluoro-substituted alkyl group or alkenyl group, a $C_1$-$C_{20}$ ester group, an ether or polyether-containing group, an alkyl- or arylamide group, an alkyl- or arylamine group, a substituted or unsubstituted $C_1$-$C_{30}$ alkoxy group, a substituted or unsubstituted $C_5$-$C_{30}$ heteroaryl group, a substituted or unsubstituted $C_3$-$C_{30}$ heterocyclic ring, a substituted or unsubstituted $C_4$-$C_{30}$ heterocycloalkyl group, a substituted or unsubstituted $C_6$-$C_{30}$ heteroarylalkyl group, a vinyl group; a $C_5$-$C_{30}$ fluoroalkyl or fluoroaryl group and combinations thereof and further wherein at least one of $T^2$ and at least one of $T^3$ are independently of the same formula as $T^1$.

11. The biomedical device of claim 9, wherein the biomedical device-forming comonomer is a silicone-containing monomer.

12. The biomedical device of claim 9, wherein the monomeric mixture further comprises a hydrophilic monomer, hydrophobic monomer or both.

13. The biomedical device of claim 9, wherein the biomedical device-forming comonomer is a hydrophilic monomer or hydrophobic monomer.

14. The biomedical device of claim 9, which is an ophthalmic lens.

* * * * *